(12) United States Patent
Santa Maria et al.

(10) Patent No.: US 11,191,667 B2
(45) Date of Patent: *Dec. 7, 2021

(54) METHOD AND SYSTEM FOR REGULATING CORE BODY TEMPERATURE

(71) Applicant: The Board of Trustees of the Leland Stanford Junior University, Palo Alto, CA (US)

(72) Inventors: Peter Santa Maria, Redwood City, CA (US); Brian Hsueh, Pacifica, CA (US); Brian Kannard, Mountain View, CA (US); Ritu Lal, Palo Alto, CA (US); Abhinav Ramani, Herndon, VA (US); John Paderi, San Francisco, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 410 days.

This patent is subject to a terminal disclaimer.

(21) Appl. No.: 15/919,953

(22) Filed: Mar. 13, 2018

(65) Prior Publication Data
US 2018/0271696 A1    Sep. 27, 2018

Related U.S. Application Data

(63) Continuation of application No. 14/197,518, filed on Mar. 5, 2014, now Pat. No. 9,956,113.
(Continued)

(51) Int. Cl.
*A61H 9/00* (2006.01)
*A61H 7/00* (2006.01)
(Continued)

(52) U.S. Cl.
CPC ............... *A61F 7/02* (2013.01); *A61H 9/00* (2013.01); *A61H 9/005* (2013.01); *A61H 9/0078* (2013.01);
(Continued)

(58) Field of Classification Search
CPC ................ A61F 7/02; A61H 9/0078; A61H 2201/0207; A61H 2201/164;
(Continued)

(56) References Cited

U.S. PATENT DOCUMENTS

267,435 A * 11/1882 Leiter ................. A61F 7/02
165/46
4,029,087 A * 6/1977 Dye .................. A61B 17/135
601/152
(Continued)

*Primary Examiner* — Tu A Vo
(74) *Attorney, Agent, or Firm* — William A. English; Vista IP Law Group LLP (57) ABSTRACT

A method for maintaining and/or increasing body temperature of a patient may involve delivering heat to a first location on a limb of the patient, delivering heat to a second location on the limb, apart from the first location, and applying intermittent compression to a third location on the limb, located between the first location and the second location. A device for maintaining and/or increasing body temperature of a patient may include a sleeve for positioning over at least part of one of the patient's limbs, first and second heat delivery members coupled with the sleeve, and an intermittent compression member coupled with the sleeve between the first and second heat delivery members.

19 Claims, 8 Drawing Sheets

Related U.S. Application Data (60) Provisional application No. 61/776,791, filed on Mar. 12, 2013.

(51) Int. Cl.
| | |
|---|---|
| *A61N 7/00* | (2006.01) |
| *A61N 1/36* | (2006.01) |
| *A61F 7/02* | (2006.01) |
| *A61H 39/00* | (2006.01) |
| *A61H 39/04* | (2006.01) |
| *A61F 7/03* | (2006.01) |
| *A61F 7/00* | (2006.01) |

(52) U.S. Cl.
CPC .............. *A61H 9/0092* (2013.01); *A61F 7/03* (2013.01); *A61F 2007/0042* (2013.01); *A61F 2007/0043* (2013.01); *A61F 2007/0045* (2013.01); *A61F 2007/0047* (2013.01); *A61F 2007/0055* (2013.01); *A61F 2007/0065* (2013.01); *A61F 2007/0086* (2013.01); *A61F 2007/0088* (2013.01); *A61F 2007/0091* (2013.01); *A61F 2007/023* (2013.01); *A61F 2007/0226* (2013.01); *A61F 2007/0239* (2013.01); *A61F 2007/0268* (2013.01); *A61F 2007/0288* (2013.01); *A61H 9/0057* (2013.01); *A61H 39/04* (2013.01); *A61H 2201/0103* (2013.01); *A61H 2201/0184* (2013.01); *A61H 2201/02* (2013.01); *A61H 2201/0207* (2013.01); *A61H 2201/0214* (2013.01); *A61H 2201/0228* (2013.01); *A61H 2201/0242* (2013.01); *A61H 2201/0278* (2013.01); *A61H 2201/164* (2013.01); *A61H 2201/165* (2013.01); *A61H 2201/1619* (2013.01); *A61H 2201/1635* (2013.01); *A61H 2201/501* (2013.01); *A61H 2201/5007* (2013.01); *A61H 2201/5097* (2013.01); *A61H 2209/00* (2013.01); *A61H 2230/50* (2013.01); *A61H 2230/505* (2013.01); *A61N 1/36042* (2013.01); *A61N 7/00* (2013.01)

(58) Field of Classification Search
CPC ........ A61H 2201/5097; A61H 2209/00; A61H 2201/0184; A61H 2201/501; A61H 2201/0214; A61H 2201/0242; A61H 2201/1635; A61H 39/04; A61H 2201/0278; A61H 2201/5007; A61H 2230/505; A61H 2201/1619; A61H 2201/0228; A61H 2201/165; A61H 9/0057; A61H 9/00; A61H 9/0007; A61H 9/005; A61H 9/0092; A61H 2201/00; A61H 2201/0103; A61H 2201/12; A61H 2201/1207; A61H 2201/16; A61H 2201/50; A61H 2201/5002; A61H 2205/00; A61H 2205/10; A61H 2205/106; A61H 2205/108; A61H 2205/12; A61H 2201/5005; A61H 2201/5056; A61H 2201/5082; A61H 2230/50
See application file for complete search history.

(56) References Cited

U.S. PATENT DOCUMENTS

| | | | | |
|---|---|---|---|---|
| 4,107,509 A * | 8/1978 | Scher | ...................... | A61F 7/007 219/527 |
| 4,865,020 A * | 9/1989 | Bullard | ................ | A61H 9/0078 601/152 |
| 5,411,541 A * | 5/1995 | Bell | .......................... | A61F 7/02 601/15 |
| 5,674,262 A * | 10/1997 | Tumey | ................. | A61H 9/0078 607/48 |
| 6,387,065 B1* | 5/2002 | Tumey | ................. | A61H 9/0078 601/152 |
| 2004/0210176 A1* | 10/2004 | Diana | ................... | A61H 9/0078 601/151 |
| 2005/0075531 A1* | 4/2005 | Loeb | .................... | A61H 9/0078 600/17 |
| 2005/0126578 A1* | 6/2005 | Garrison | ............. | A61M 16/024 128/874 |
| 2006/0004245 A1* | 1/2006 | Pickett | ................. | A61H 31/008 600/16 |
| 2007/0060988 A1* | 3/2007 | Grenon | ..................... | A61F 9/00 607/96 |
| 2008/0021531 A1* | 1/2008 | Kane | ...................... | A61H 9/005 607/111 |
| 2008/0064992 A1* | 3/2008 | Stewart | ................. | A61H 9/0078 601/7 |
| 2008/0132976 A1* | 6/2008 | Kane | ..................... | A61H 9/0007 607/104 |
| 2008/0249444 A1* | 10/2008 | Avitable | ................. | A61H 1/008 601/152 |
| 2009/0069731 A1* | 3/2009 | Parish | ................... | A61F 7/0085 601/150 |
| 2009/0177184 A1* | 7/2009 | Christensen | ......... | A61H 9/0057 604/506 |
| 2009/0227922 A1* | 9/2009 | Nardi | ...................... | A61F 13/06 601/152 |
| 2009/0260639 A1* | 10/2009 | Hsu | ...................... | A61F 13/0213 128/888 |
| 2009/0270910 A1* | 10/2009 | Hargens | ................ | A61H 9/005 606/201 |
| 2010/0042027 A1* | 2/2010 | Hirata | ................. | A61F 5/05816 601/151 |
| 2010/0152821 A1* | 6/2010 | Rein | ..................... | A61H 9/005 607/96 |
| 2010/0210982 A1* | 8/2010 | Balachandran | ....... | A61F 7/0085 601/152 |
| 2011/0004132 A1* | 1/2011 | Cook | ................... | A61H 9/0092 601/152 |
| 2011/0098792 A1* | 4/2011 | Lowe | ....................... | A61F 7/02 607/104 |
| 2011/0190675 A1* | 8/2011 | Vess | .................... | A61H 9/0092 601/152 |
| 2011/0251536 A1* | 10/2011 | Wilford | .................... | A61H 9/00 601/151 |
| 2012/0041351 A1* | 2/2012 | Nolan | ................... | A61F 13/085 602/13 |
| 2012/0065561 A1* | 3/2012 | Ballas | .................... | A61H 9/0078 601/152 |
| 2013/0030331 A1* | 1/2013 | Quisenberry | ........... | A61F 7/007 601/18 |
| 2013/0310719 A1* | 11/2013 | Davis | .................... | A61H 9/0085 601/149 |
| 2014/0222121 A1* | 8/2014 | Spence | .................... | A61F 7/02 607/104 |

* cited by examiner

METHOD AND SYSTEM FOR REGULATING CORE BODY TEMPERATURE

CROSS-REFERENCE TO RELATED APPLICATIONS

The present application is a continuation of co-pending application Ser. No. 14/197,518, filed Mar. 5, 2014, which claims benefit of U.S. provisional application Ser. No. 61/776,791, entitled "Method and System for Regulating Core Body Temperature," filed Mar. 12, 2013, the entire disclosures of which are expressly incorporated by reference herein.

STATEMENT REGARDING FEDERALLY SPONSORED RESEARCH AND DEVELOPMENT

This invention was made with Government support under contract TR001085 awarded by the National Institutes of Health. The Government has certain rights in the invention.

FIELD OF INVENTION

The present application relates to medical devices and methods. More specifically, the application relates to methods, devices and systems for regulating body temperature of a mammal.

BACKGROUND

Each year, over 60 million surgical procedures are performed in the United States. While great care is taken to prevent surgical complications, one overlooked and under-addressed problem is the risk of developing hypothermia before, during or after surgery (referred to as "inadvertent perioperative hypothermia" or "IPH"). Patient temperatures can drop precipitously during surgery, due to the effects of general anesthesia, lack of insulating clothing, and exposure to cold operating room temperatures. Even with today's standard of care, 30-50% of surgical patients will develop hypothermia.

Hypothermia often causes much more than patient discomfort. Patients who suffer even mild hypothermia are at significantly elevated risk for developing surgical site infections, cardiac morbidities, and other complications. Together, these significantly increase recovery time and overall length of hospital stay, leading to increased costs for all parties. By some estimates, unmanaged risk for IPH is a $15 billion problem in the United States alone, and yet is largely overlooked.

Perioperative heat loss occurs predominantly via convective heat transfer, particularly through the palms of the hands and soles of the feet. During preoperative care, patients are dressed solely in a gown and are often exposed to cold waiting areas with little insulation. Therefore, although patients are only anesthetized during surgery, patients often arrive to the surgical theater already slightly hypothermic. This puts a patient under greater risk for developing hypothermia once anesthesia has been administered. Postoperative drops in core temperature increase the likelihood of developing additional morbidities, such as morbid cardiac outcomes, surgical site infections, and blood loss, any of which typically prolongs recovery and hospitalization.

Patients undergoing surgery are very likely to develop hypothermia during the surgical procedure itself, especially when the procedure involves their core area, such as procedures involving the thoracic, abdominal, and pelvic regions. Surgeries of the core involve the exposure of vital internal organs to the cooler environment and thus carry a greater risk of hypothermia. Furthermore, core surgeries often necessitate the uncovering of the trunk and chest, which render blankets and many other existing interventions inadequate. Once in the operating room, patients are naked and exposed to a room temperature well below 36 degrees Celsius and to cold liquids used to wash the surgical site during sterilization preparation. At the onset of surgery, delivered anesthetics immediately impair the normal autonomic thermoregulatory controls. Colder blood is transferred from the peripheries of the body to the core through a phenomenon known as redistributive hypothermia. Vasodilatation and reduction in muscle tone cause a significant drop in core temperature within the first half-hour of surgery.

The development of IPH is strongly correlated with a multitude of physiological organ system changes, impacting the cardiovascular, respiratory, neurologic, immunologic, hematologic, drug metabolic, and wound healing mechanisms. The incidence of several post-surgical complications is increased due to even mild hypothermia. Intraoperatively, hypothermia can cause a decrease in cardiac output and heart rate, which can lead to ventricular dysrhythmias. Platelet functions become impaired and there is a decrease in coagulation factors, which leads to greater intraoperative bleeding and blood loss. Impaired immune functions increase the rate of surgical site infections. Hypothermia is associated with a four-fold increase in surgical would infection and twice as many morbid cardiac events. These complications and others are supported in multiple studies and result in both clinical and economic burdens.

Overall, compared to non-hypothermic patients, those who suffer IPH experience greater rates of surgical site infections, bleeding, cardiac complications which may require additional monitoring, PACU length of stay, total length of stay, and subjective discomfort. Although it is counterintuitive, the likelihood of developing hypothermia in an open versus laparoscopic surgery is similar across various types of procedures, most likely attributable to the fact that most laparoscopic procedures are significantly longer when compared to their open surgery counterpart.

Current methods of preventing hypothermia are not completely effective. Even with the current interventions, up to 46% of patients are reported to be hypothermic at the start of surgery and 33% are hypothermic upon arrival to the PACU. Assuming the cost savings for maintaining normothermia in one patient is approximately $5,000 per patient, and approximately 30% of the 17 million high-risk surgical patients are hypothermic, a system-wide cost savings of $15 billion will be realized by keeping these patients normothermic. With rising healthcare costs and recent initiatives by CMS mandating the maintenance of perioperative normothermia, hospital administrators nationally are in need of new, efficacious and cost-effective devices to address perioperative hypothermia, a product space which has seen little innovation since the introduction of the forced air warming blanket nearly three decades ago.

Currently available devices for perioperative warming are primarily forced air warming blankets. In particular, the Bair Hugger™ device (Arizant Healthcare, Inc.) is the most commonly used technology and is used in 85% of U.S. hospitals. Newer alternatives include high-heat transfer conduction heating blankets and intraoperative hand warming devices. Although these devices are somewhat effective, they all have several key shortcomings: (1) They are cumbersome, and thus compliance and correct usage is low; (2)

Warming in the intraoperative period alone is significantly less effective than warming preoperatively and intraoperatively; and (3) Devices that heat via the core of body are ineffective during surgeries of that anatomical area. Currently available devices are often not used or not practical for use in preoperative warming for one or more of the following reasons: (1) They immobilize the upper limbs; (2) They are cumbersome—e.g., they float on the patient and get blown off during implementation and transport and they require large, predominantly floor-based blowers that are not mobile; (3) They are not attached to the patient and become dislodged during transport and obstruct the bed and other monitors and devices; and/or (4) They require a conscious administrative decision to implement. This has been shown to take up to 30 minutes to deploy effectively in clinical studies. A busy and stressed preoperative nurse cannot afford this time.

Additionally, currently available patient warming devices are often not used for any of the above reasons and/or any of the following reasons: (1) Fear of contaminating surgical field—e.g., forced air methods can blow bacteria containing air onto the surgical field; (2) Forced air blankets get in the way—e.g., to warm the core, they need to be in contact with the core; and/or (3) Operating room staff may turn down the temperature on the device due to their own comfort—e.g., operating room staff turns down the patient's forced air due to air escape heating the surrounding staff.

Therefore, it would be advantageous to have improved methods and systems for maintaining a patient's core body temperature before, during and/or after surgery. Ideally, such methods and systems would be easy to set up and use, unobtrusive and effective. Also ideally, such methods and systems would be suitable for use before, during and after a surgical procedure and would be acceptable to the patient while awake in the preoperative and postoperative settings. At least some of these objectives will be met by the embodiments described herein.

SUMMARY

Devices, systems and methods described herein are directed toward delivering thermal energy and/or blood flow regulating therapy to a patient to help regulate body temperature. In many embodiments, a device, system and method involves delivering both thermal energy and blood flow regulating therapy to the body. Blood flow regulation is typically used in the systems, devices and methods described herein to help return blood to the core of the body from one or more extremities. This blood flow regulation therapy may be accomplished in a number of different ways, such as but not limited to intermittent compression and/or electrical stimulation. In some embodiments, a device is applied to a lower or upper limb, and the device delivers heat to at least one area and blood flow regulation therapy to at least one area on the lower limb. In one specific embodiment, for example, a body temperature regulation device may deliver heat to two different areas on a limb and intermittent compression near the one or both of the two areas. In one specific embodiment, heat is delivered to the popliteal fossa (posterior aspect of the knee) and sole of the foot, and intermittent compression is delivered to an area between the popliteal fossa and the foot.

In one aspect, a method for maintaining or increasing body temperature of a patient may involve delivering heat to a first location on a limb of the patient, delivering heat to a second location on the limb, apart from the first location, and applying intermittent compression to a third location on the limb, located between the first location and the second location. In some embodiments, the limb is a lower limb, the first location is a popliteal fossa of the lower limb, and the second location is a sole of a foot of the lower limb. In some embodiments, the heat is delivered and the compression is applied to both lower limbs of the patient. In some embodiments, the heat and compression may be delivered and applied to the first, second and third locations at the same time. Alternatively, the heat and compression may be delivered and applied to the first, second and third locations at at least two different starting times and/or for at least two different lengths of time.

In some embodiments, the heat delivery and compression application steps are performed by one device having heat delivery and intermittent compression capabilities. In alternative embodiments, the heat delivery and compression application steps may be performed by multiple devices. Optionally, these multiple devices may be connected to a common control unit configured to control operation of the multiple devices.

The method may optionally further involve adjusting positioning of at least a portion of at least one of a heat delivery device or a compression device on the limb to change at least one of the first location, the second location or the third location. In various embodiments, the heat may be delivered in the form of ultrasound, electrical, mechanical, chemical, radiative and/or convective energy. In various embodiments, applying intermittent compression may involve applying electrical stimulation, mechanical compression and/or acupuncture.

In some embodiments, the method may further involve measuring a temperature of the patient, a temperature of a heat delivery device and/or an amount of compression applied to the patient. Such a method embodiment may optionally further involve adjusting at least one of the heat delivery or the intermittent compression, based on the measurement. The method may further involve, before the heat delivery and compression application steps, placing a sleeve over at least part of the limb, where the sleeve includes heating and compression members. The method may also optionally involve forming a vacuum between the sleeve and the limb, before delivering the heat or applying the compression.

In various embodiments, the heat delivery and compression application steps may be performed during a time period before a surgical procedure is performed on the patient, during performance of the surgical procedure on the patient, and/or after performance of the surgical procedure on the patient. In some embodiments, the method may be performed on a patient who has a condition such as but not limited to lymphedema, deep vein thrombosis, peripheral artery disease, muscular conditions or disorders, or a heightened risk of any of these conditions.

In another aspect, a device for maintaining or increasing body temperature of a patient may include a sleeve configured for placement over at least a portion of a foot and a portion of a leg of the patient, a first heat delivery member coupled with the sleeve such that it is positioned over a popliteal fossa of the patient when the sleeve is placed over the leg, at least a second heat delivery member coupled with the sleeve such that it is positioned over a sole of the foot when the sleeve is placed over the foot, and at least one intermittent compression member coupled with the sleeve such that it is positioned in an area between the first and second heat delivery members when the sleeve is placed over the leg and the foot. In various embodiments, the heat delivery members deliver energy in a form of ultrasound, electrical, mechanical, chemical, radiative or convective energy. In some embodiments, the intermittent compression member comprises at least one expandable bladder. Alternatively, the intermittent compression member may include at least one pressure chamber.

Optionally, the device may also include a controller coupled with the sleeve for controlling at least one of heat delivery or compression application by the device. Such embodiments may also optionally include least one temperature sensor for sensing a temperature of the patient, and a connection between the at least one temperature sensor and the controller to provide sensed temperature data to the controller. In some embodiments, the controller may include a feedback loop configured to control the heat delivery members and the compression member, based on the sensed temperature data.

The sleeve may include multiple compartments, and the heat delivery members and the intermittent compression members may be disposed in the compartments. In some embodiments, at least one of the heat delivery members is moveable relative to its location on the sleeve to adjust its location on the limb. Optionally, the intermittent compression member may also be moveable relative to its location on the sleeve to adjust its location on the limb. The first heat delivery member, the second heat delivery member and/or the intermittent compression member may be longitudinally moveable relative to the other members along the sleeve to adjust locations of the members relative to one another, in some embodiments.

The device may also include a wicking material on an inner surface of at least part of the sleeve to help wick moisture away from skin of the limb. The device may also include a suction device coupled with the sleeve to provide a vacuum between an inner surface of the sleeve and the limb. The device may also include an adhesive on at least a portion of an inner surface of the sleeve to provide adhesion between the inner surface and skin of the limb. All of these are optional features, which may be included on various embodiments.

In another aspect, a system for maintaining or increasing a body temperature of a patient may include: a first heat delivery member configured for positioning over a popliteal fossa of a lower limb of the patient; at least a second heat delivery member configured for positioning over a sole of the foot of the lower limb; at least one intermittent compression member configured for positioning on the lower limb between the popliteal fossa and the foot of the limb; at least one heat source couplable with the first and second heat delivery members; and at least one compression source couplable with the at least one intermittent compression member. Optionally, the system may also include a sleeve configured for placement over at least a portion of the lower limb, including at least a portion of the foot and the popliteal fossa, where the first heat delivery member, the second heat delivery member and the intermittent compression member are coupled with the sleeve.

The system may also include at least one connector for connecting the heat source with the first and second heat delivery members and for connecting the compression source with the at least one compression member. For example, the at least one connector may comprise multiple connectors joined together along at least a portion of their lengths. In some embodiments, the system may also include a controller coupled with the at least one heat source and the at least one compression source, for controlling delivery of heat and application of compression to the leg and the foot. In some embodiments, the controller, the at least one heat source and the at least one compression source are housed in one, combination device. In some embodiments, the combination device may be configured to attach to a side of a bed. Optionally, the system may further include at least one temperature sensor for sensing a temperature of the patient and at least one connector connecting the at least one temperature sensor to the controller, so that the sensed temperature can be conveyed to the controller.

These and other aspects and embodiments will be described in further detail below, in references to the attached drawing figures.

DETAILED DESCRIPTION

The following disclosure describes various embodiments of a method, device and system for regulating body temperature of a mammal. The various embodiments generally combine delivery of heat with delivery of blood flow regulation therapy to increase and/or maintain body temperature. Although the blood flow regulation therapy most described below is intermittent compression, in alternative embodiments, different types of blood flow regulation therapy may be used, such as electrical stimulation. The embodiments are typically, though not necessarily, configured for use on a limb of a patient. Although the following descriptions focus primarily on use of the methods, devices and systems on a lower limb (i.e., leg and foot) of a human patient, in alternative embodiments, the methods, devices and systems may be used on an upper limb, on a lower limb and upper limb, on two lower or two upper limbs or any other combination. In still further embodiments, methods, devices and systems may be alternatively or additionally used on a torso or other anatomical region of a patient. Additionally, although the embodiments are generally described for use in delivering heat to maintain and/or increase body temperature, alternative embodiments may be used for cooling the body.

Figure 1:
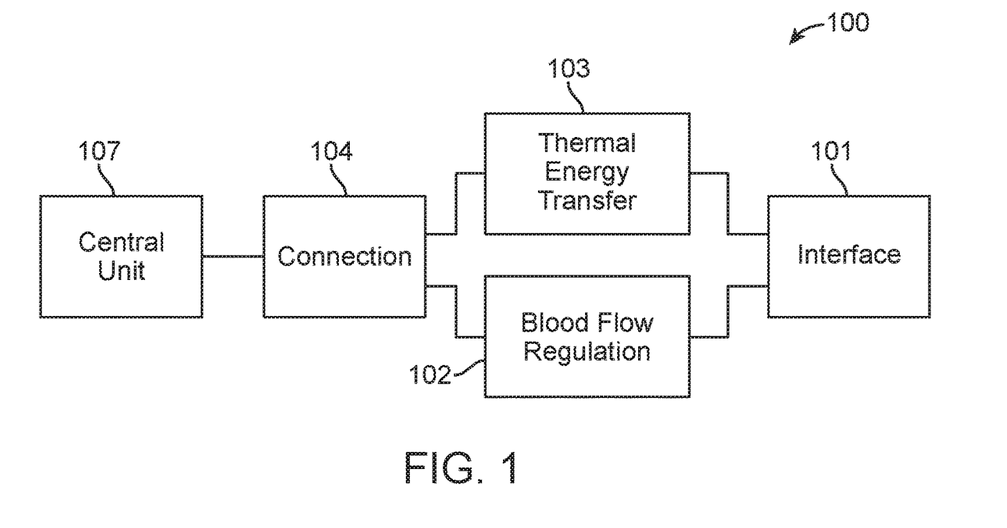
FIG. 1 is a diagrammatic representation of a body temperature regulation system, according to one embodiment.
Figure 2:
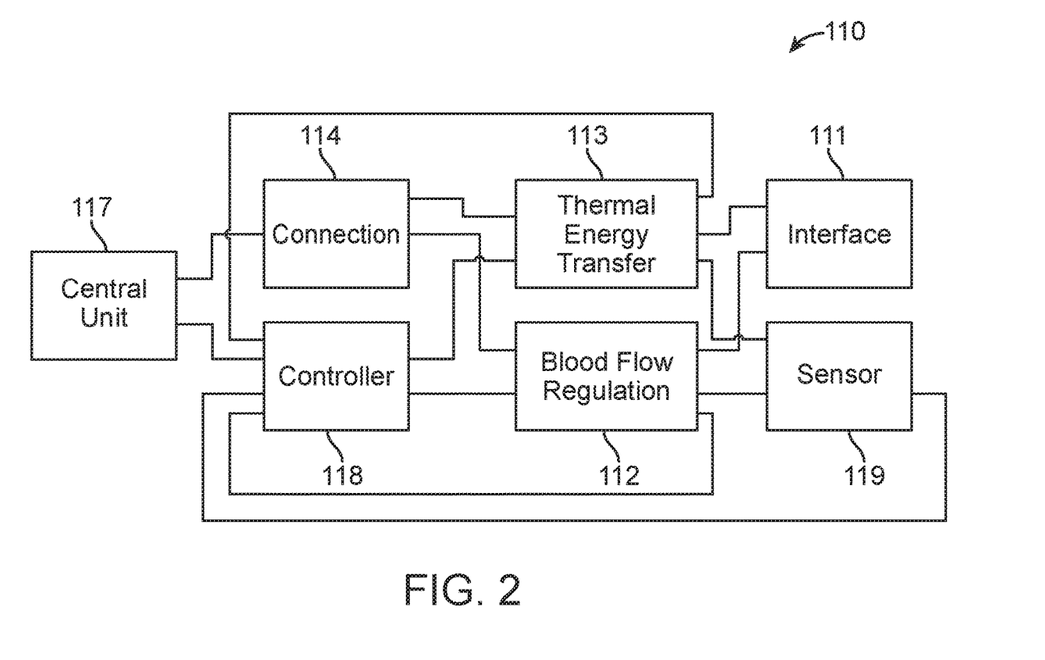
FIG. 2 is a diagrammatic representation of a body temperature regulating system, according to an alternative embodiment.

FIGS. 1 and 2 are diagrammatic depictions of two embodiments of a body temperature regulating system. Referring now to FIG. 1, in one embodiment, a body temperature regulating system 100 may include a body interface member 101, a blood flow regulation member 102, a thermal energy transfer member 103, a connector 104 and a central unit 107. Each of these components of system 100 may be single components or multiple components, according to various embodiments. For example, body interface member 101 may be one sleeve that fits over a limb or multiple sleeves, according to alternative embodiments. Blood flow regulation member 102 may be one heat delivery device or multiple heat delivery devices, according to alternative embodiments. The same is true of the other components. Therefore, although each component is referred to herein in the singular, each may actually include multiple devices, components, parts or the like.

Body interface member 101 is configured to attach to a patient and to contain or otherwise attach to blood flow regulation member 102 and thermal energy transfer member 103. All of these features will be described in further detail below. In general, in some embodiments, body interface member 101 may include one or more sleeves that fit over at least a portion of a lower limb (or upper limb in alternative embodiments). Blood flow regulation member 102 may include one or more compression members for delivering compression to a portion of the body with which it comes into contact. In some embodiments, this compression is delivered intermittently. Thermal energy transfer member 103 may include one or more heat delivery members for delivering heat to one or more areas of the limb. In one embodiment, for example, body interface member 101 may fit over a portion of the lower limb, including at least part of the popliteal fossa, at least part of the sole of the foot, and an area between the two. Thermal energy transfer member 103 may include a heat delivery member at the popliteal fossa and another heat delivery member at the sole of the foot. Blood flow regulation member 102 may include one intermittent compression member attached to body interface member 101 in a location between the two heat delivery members of thermal energy transfer member 103. This is only one example, however, and many alternatives are possible.

Connector 104 may include any suitable connector or combination of connectors for transferring any combination of thermal energy, electrical power, a fluid, data and/or the like between body interface member 101 and central unit 107. Central unit 107 may include, for example, a source of thermal energy, a source of compression force, or both. Intermittent compression may be delivered in the form of air that inflates a bladder of blood flow regulation member 102, for example. In some embodiments, central unit 107 may include two or more separate devices, such as a thermal energy source and a separate source of compression force. In alternative embodiments, central unit 107 may be only one device. In alternative embodiments, system 100 may include only thermal energy transfer member 103, only blood flow regulation member 102, or any combination of components.

With reference now to FIG. 2, an alternate embodiment of a body temperature regulating system 110 may include a body interface member 111, a blood flow regulation member 112, a thermal energy transfer member 113, a connector 114 and a central unit 117, as described in relation to the embodiment above. Additionally, system 110 may include a control unit 118 and a sensor 119. Sensor 119, for example, may sense a patient's body temperature, the temperature of a heat delivery member, and/or the like. Any suitable temperature sensor may be used, and any suitable number of sensors may be attached to interface member 111, for example. Control unit 118 may be coupled with, and may receive sensed information from, sensor 119. Control unit 118 may then transmit signals to central unit 117 to adjust delivery of heat and/or compression to a patient, according to the sensed temperature data from sensor 119. In many embodiments, control unit 118 may be combined with central unit 117 in one device or "box." For example, one device or box may be used, in some embodiments, to (1) deliver thermal energy, (2) deliver intermittent compression force, and (3) control the delivery of thermal energy and compression. In some embodiments, the same device or box may also be used to receive sensed signals from one or more sensors and use those signals as feedback for controlling the delivery of thermal energy and compression. In other embodiments, any one or more of these functions may be performed by one or more separate devices.

FIGS. 1 and 2 are block diagrams, illustrating components of two embodiments of a system 100, 110 for regulating patient temperature. In alternative embodiments, components may be added, removed or changed, and/or connections of the components may be altered. In some embodiments, one component of the system may be provided separately as a device for use with another system or device. Furthermore, in various embodiments, the system may be placed on a single, multiple, or any combination of extremities of the body where peripheral blood flow is present. The word "extremities," as used herein, refers to the arms, legs, head and neck. As mentioned previously, in various embodiments, the systems described herein may be applied to any extremity, portion of an extremity or combination of multiple extremities. Alternative embodiments may be used with other parts of a patient, such as the trunk. Therefore, although the following description focuses on various embodiments for use on one or both lower limbs of a patient, these embodiments are provided only as examples.

Figures 3A, 3B:
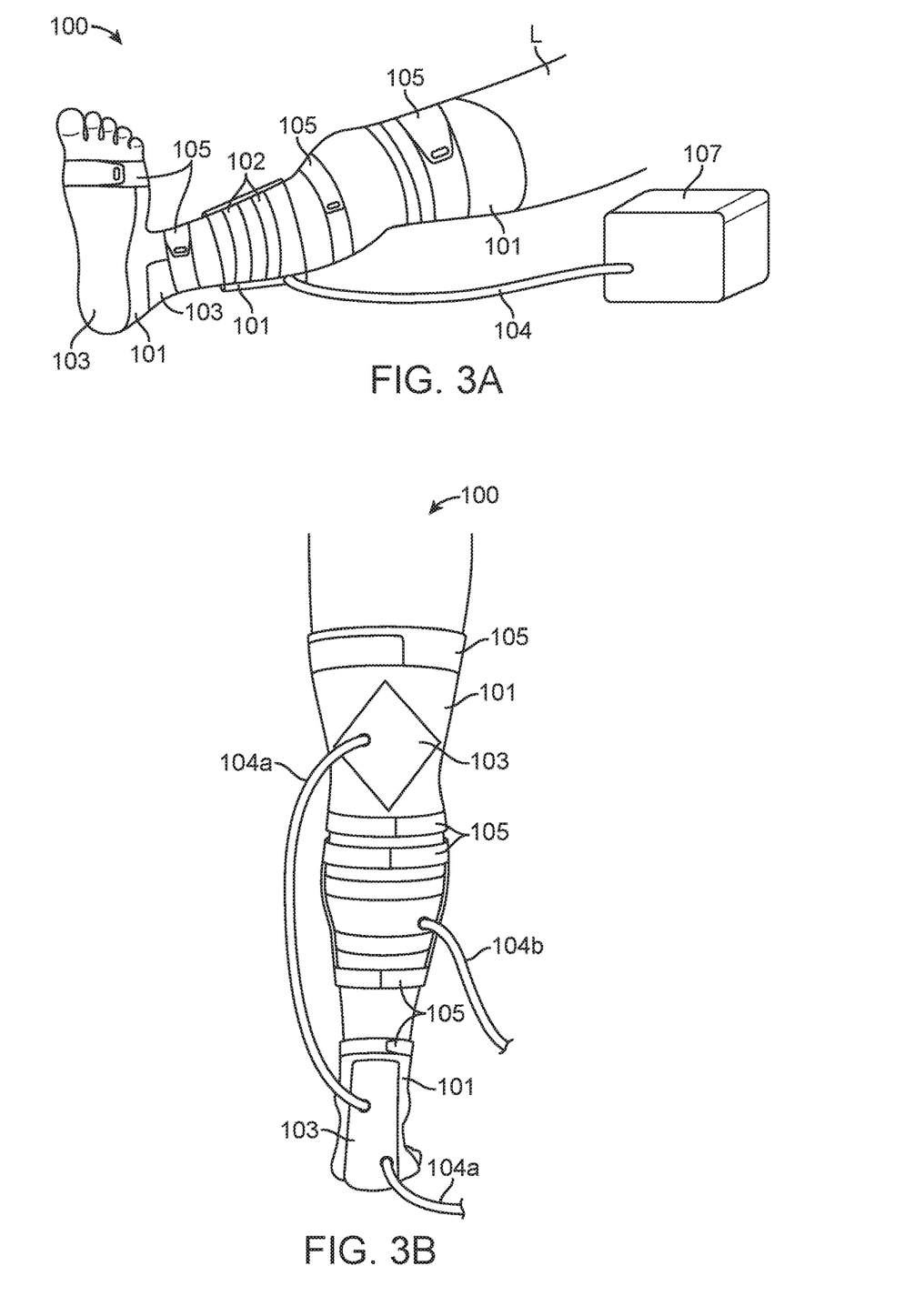
FIGS. 3A and 3B are perspective and posterior views, respectively, of a lower limb of a human with a body temperature regulation system in place on the lower limb, according to one embodiment.

Referring now to FIGS. 3A and 3B, perspective and posterior views, respectively, of a portion of a human leg L illustrate one embodiment of temperature regulation system 100 in a position for use. Body interface member 101, in this embodiment, includes multiple sleeves that fit over the leg L and foot of the patient, and that are attached via multiple straps 105, such as Velcro straps. Thermal energy member 103 includes two heat delivery devices (each labeled 103), which are attached to interface member 101 so as to be located at the popliteal fossa (posterior portion of the knee) and on a portion of the sole of the foot. Blood flow regulation member 102 includes one intermittent compression delivery device attached to interface member 101 so as to be located between the two thermal energy members 103. Central unit 107 is connected to the rest of system 100 via connector 104, to provide thermal energy delivery and compression force delivery. In FIG. 3, connector 104 is illustrated for simplicity as one connector 104. However, in embodiments like the one shown, where there are three separate body interface members 101 and thus three separate components to provide thermal energy and compression, three connectors 104 would actually be connected to central unit 107 to provide thermal energy and compression to the three separate components.

In use, thermal energy is transferred from thermal energy transfer members 103 through the tissue to the peripheral arterial and venous blood. Alternately, the energy transfer may flow in the opposite direction, from the peripheral blood through the tissue to the thermal energy transfer members 103 (e.g., to reduce body temperature). Through the transfer of thermal energy in the peripheral blood, the core body temperature may be regulated as the peripheral blood returns to the core. Locating thermal energy transfer members 103 in locations on the body where thermal energy transfer to the peripheral blood is most efficient can improve the efficiency the system. This allows for sufficient thermal energy transfer while minimizing the body surface area required for device coverage. In various alternative embodiments, locations for positioning thermal energy transfer members 103 may include the entire extremity or may be limited to the popliteal fossa, sole of the foot, ankle, groin, palm of the hand, wrist, armpit, neck, head, or any portion(s) or combination(s) of these locations.

The various embodiments of systems and methods for the transfer of thermal energy to the body described herein may include any means of introducing or extracting thermal energy. Specific examples of thermal energy introduction include electrical energy, electromagnetic energy including light, lasers, radiation, or induction, convective transfer through a liquid such as air or water, chemical energy such as from an exothermic chemical reaction, acoustic energy such as ultrasound or high-intensity focused ultrasound (HIFU), mechanical energy such as vibration, or any other energy transfer method/system now known or discovered in the future. Additionally, in some embodiments, the systems and methods may induce physiological thermal production through an increase in metabolism and/or by stimulating physiological responses from blunt or sharp trauma. Thermal energy may be efficiently extracted from the body through the use of a heat sink or heat sinking materials, or by the application of cold media to the body.

In various embodiments, body interface member 101 (multiple pieces in the embodiment of FIGS. 3A and 3B) may be made of any suitable material. Ideally, such material will be breathable and/or repel moisture. Some examples of materials may include, but are not limited to, polyethylene, polyvinyl chloride, or other polyesters, either woven or non-woven. In some embodiments, the regulation of core body temperature via thermal energy transfer members 103 may be enhanced through the modulation of peripheral blood flow via one or more blood flow regulation members 102. Blood flow regulation member 102, which in the pictured embodiment comprises an intermittent compression device, may be a part of system 100 applied to the leg L or other extremity. By regulating the venous return of the peripheries in which thermal energy has been transferred, system 100 can enhance its thermal regulation of the body core. This can increase the efficiency of system 100 and allow for regulation of the core body temperature with a smaller, less intrusive system located on the extremities of the body.

As just mentioned, blood flow regulation member(s) 102 may provide for the application of force or compression to the muscles of the extremity in order to enhance the venous return. In some embodiments, blood flow regulation member(s) 102 include intermittent compression devices, such as air bladders with compartments that fill and empty repeatedly to squeeze the body tissue. As this type of air bladder intermittent compression device is well known currently, it will not be described further here. However, any such currently known intermittent compression bladder device or any such device developed in the future may be used in various embodiments of system 100.

In various alternative embodiments, blood flow regulation member(s) 102 may include sequential compression devices, mechanical squeezing or force application through tightening of a sleeve around the extremity, mechanical alteration or stretching of skin, delivery of one or more pharmacological agents, or a combination thereof. Any of these embodiments may include one or multiple chambers filled with a fluid, such as air, water, or a high specific heat gas or liquid. Blood flow regulation member(s) 102 that provide for application of force may be intermittent or continuous. Intermittent compressive force may include sequential application, including random or patterned application or wave application, including sinusoidal, square, forward and/or reverse wave patterns.

In alternative embodiments, blood flow regulation may additionally or alternatively involve causing local vasodilation, and blood flow regulation member(s) 102 may include one or more devices designed to promote vasodilation. Blood flow regulation member(s) 102 for promoting local vasodilation may act through a metabolite, a hormone, or the nervous system, creating hypoxia, or the application of a vacuum, for example. In other alternative embodiments, blood flow regulation may additionally or alternatively involve promoting muscle contraction. Such methods may include active stimulation such as electrical muscle stimulation or acting on the peripheral nervous system. Alternatively, methods may include passive contraction through pharmacological means or through applied movement to the extremity.

With continued reference to FIG. 3, system 100 may be applied to the body (leg L or other extremity) by way of body interface member 101, which may include one or more housings and/or one or more sleeves. Interface member 101 is generally configured to provide stability, comfort, and ease of motion for ambulatory patients, as well as proper fit and interface between system 100 and the body. This helps ensure proper function of other components in system 100, including thermal energy transfer member 103 and blood flow regulation member 102. Interface member 101 may include and enclose body worn electronics for a mobile and wireless system, including but not limited to a power source, circuit board, sensors such as temperature and pressure, and/or wireless communication devices. It may also include pipes, tubing, one or multiple pumps, heating elements, cloth, and/or other components. Body interface member 101 may include a sleeve, blanket, wrap, patch and/or the like. Proper fit and function may be ensured through the use of adhesives or stickers. Additionally, body interface member 101 may include a portion, or multiple portions, that extend internally into the patient, for example into a subdermal or subcutaneous layer of the body. Body interface member 101 may be multi-layered, providing thermal or electrical insulation, thermal or electrical conduction, force application, electrical connection, or other features in different layers of the interface. In various alternative embodiments, the components of system 100 may be housed in a single or multiple enclosures of body interface member 101, such as pockets. The components of system 100 may directly contact the patient's skin in some embodiments, and alternatively there may be a layer of body interface member 101 between one or more of the components and the skin, for example if one or more components are housed in one or more pockets of body interface member 101. Also in various alternative embodiments, body interface member 101 may be worn directly on the skin surface or externally/outside of clothing.

Body interface member 101 may be attached to the patient's leg L or other extremity by any suitable means, such as but not limited to one or more attachment members coupled with interface member 101. In the embodiment shown in FIG. 3, for example, multiple straps 105 are used as a means to ensure system 101 is easy to apply, remains in place during the working life, and is easy to remove when necessary. System 100 may include straps or other attachment means that use Velcro, magnets, string, ties, clips, elastic bands and/or the like. System 100 also includes one or more connectors 104, to transfer any combination of thermal energy, electrical power, a fluid, and/or data between body interface member 101 and central unit 107. For simplicity of illustration, only one connector 104 is illustrated in FIG. 3A. In FIG. 3B, three connectors 104 are shown—two connectors 104a for delivering thermal energy to thermal energy transfer members 103, and one connector 104b for delivering compression force to blood flow regulation member 102. In various embodiments, connectors 104a, 104b may connect with one central unit 107 or with multiple devices. Connectors 104 may also transmit sensed data from one or more sensors 119 (not shown) on body interface unit 101 to central unit 107. For example, one or more temperature sensors may be coupled with body interface unit 101 to sense body temperature. Central unit 107 may be body worn on the patient in some embodiments or located separate from the patient, as shown. Connectors 104 and central unit 107 may be separate for each device located on a different extremity or combined for an entire system acting on one or multiple extremities.

As discussed above in reference to FIG. 2, system 100 may include other components as well. These include but are not limited to controller 118 and one or more sensors 119 (neither of which is shown in FIGS. 3A and 3B). Sensors 119, such as temperature sensors, may measure core, peripheral, skin, tissue, and/or blood temperatures. Information transmitted from sensors 119 to controller 118 may be used by controller to adjust system 100 to modulate thermal energy transfer. Additionally or alternatively, one or more sensors 119 may be configured to determine blood flow, and controller 118 may also use such blood flow information to adjust system 100. Controller 118 may act in system 100 to control the function and/or output of other components, including but not limited to thermal energy transfer members 103 and/or blood flow regulation member 102. Controller 118 may receive data and feedback from the components it is controlling and may also receive data and feedback from sensors 119.

Sensors 119 may provide for data acquisition to determine the functionality and effects of system 100. Specifically, such data may include, but is not limited to, temperature data such as core, peripheral, skin, tissue, and/or blood temperature. This data may be provided to controller 118, thermal energy transfer member 103, a user interface internal or external to system 100 (laptop computer, desktop computer, or the like, for example), a data acquisition device internal or external to system 100, another component or piece of equipment internal or external to system 100, or any combination of these. Similarly, other data may be acquired by sensors 119, including blood flow measurements, and utilized in a similar manner to that described for temperature sensors.

Additionally, system 100 may include a user interface (not shown) to provide a means in which a user can turn on or off different components of system 100 or input settings such as desired temperature and to allow system 100 to output data to a user such as temperature or blood flow settings and/or readings. System 100 may also provide feedback to the user that may include alarms, data, information, or messages given via a screen, light, sound, or tactile feedback. System 100 may additionally include communication equipment to allow various system components to communicate in wired or wireless fashion and/or to allow communication between system 100 and other, external devices or systems, including hospital equipment, computers, printers, etc. System 100 may also include a power source, which in some embodiments may be coupled directly with another component of system 100 and worn by the patient, thus not requiring attachment to any power outlet. Such a power source may include one or multiple batteries, for example. System 100 may also include the ability to switch between battery and outlet power to allow for mobile and ambulatory use. System 100 may also utilize other sources of power, such as but not limited to power from the building supply or wireless power such as inductive power, solar, or power derived from mechanical movement.

In various alternative embodiments, system 100 may include any suitable combination of the components described above. In some embodiments, in fact, one single component may be provided as a device, which may be coupled with and used with system 100 or some other, alternative system. Specifically, various embodiments of system 100 may include one or more thermal energy transfer members 103 only, one or more blood flow regulation members 102 only, a combination of thermal energy transfer member(s) 103 and blood flow regulation member(s) 102 components as part of the same system, a combination of thermal energy transfer member(s) 103 and blood flow regulation member(s) 102 as part of separate devices, thermal energy transfer member(s) 103 used in conjunction with other existing devices, including those meant to regulate blood flow, or any other combination of the components described herein. These may include a device consisting of one or multiple thermal energy transfer members 103 that can be worn with existing deep vein thrombosis (DVT) prophylaxis devices, such as compression socks or sequential compression devices (SCD) or similar devices for other conditions. Therefore, the descriptions of embodiments herein as "devices" and/or "systems" should not be interpreted as limiting the scope of the invention due to any particular use of the terms "device" and "system."

Figure 4A:
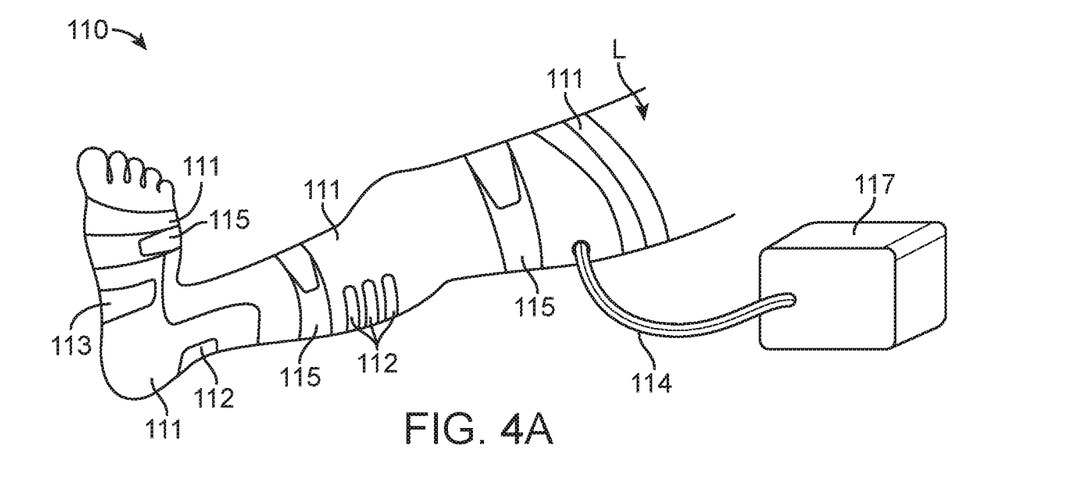
FIGS. 4A and 4B are perspective and posterior views, respectively, of a lower limb of a human with a body temperature regulation system in place on the lower limb, according to an alternative embodiment.
Figure 4B:
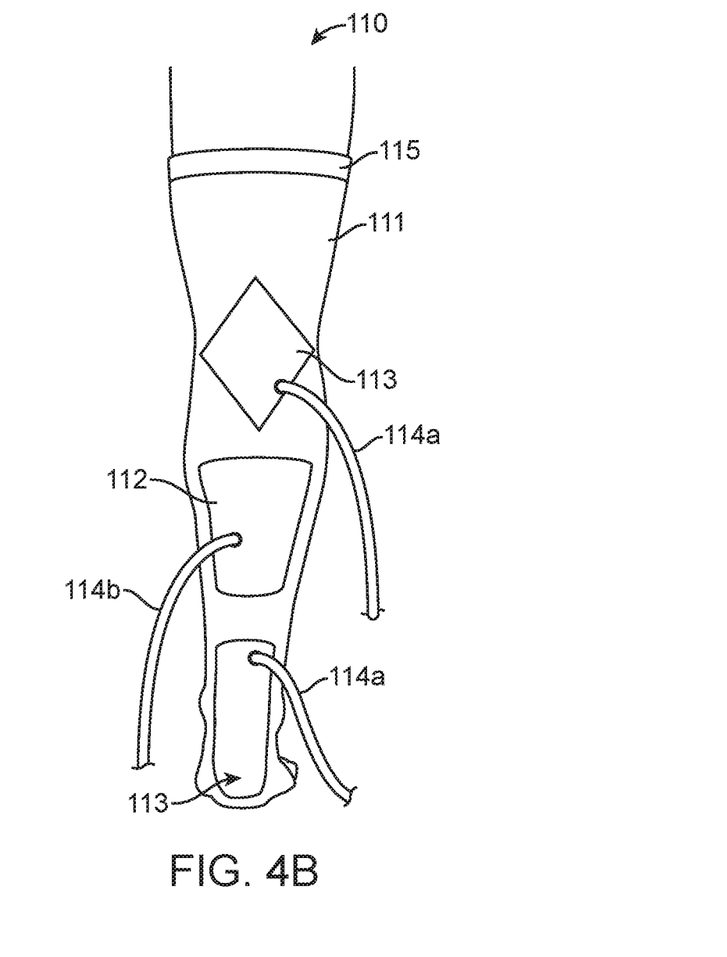

Referring now to FIGS. 4A and 4B, in an alternative embodiment, a body temperature regulation system 110 may include all the same components as described in relation to the previous embodiment, except that a body interface member 111 may be one, continuous sleeve, rather than multiple sleeves. Such a sleeve/interface member 111 may be pulled on over the foot and up onto the leg L, like a long sock. Such an interface member 111 may be made of any suitable material. Ideally, such material will be breathable and/or repel moisture. Some examples of materials may include, but are not limited to, polyethylene, polyvinyl chloride, Neoprene, elastic, nylon, Spandex, other polyesters, combinations of any of these materials or the like. Interface member 111 may also be either woven or non-woven. Straps 115, such as Velcro straps, may be used to further secure interface member 111 with the skin. Coupled with interface member 111 are thermal energy transfer members 113, blood flow regulation member(s) 112, connector 114 and central unit 117. Although multiple connectors 114a and 114b are illustrated in FIG. 4B, in one embodiment these connectors 114a, 114b may be combined into one connector 114, as illustrated in FIG. 4A. In such a one-connector embodiment, thermal energy and/or compression force or other blood flow regulation energy may be transferred through body interface member 111 to the various components. Not shown, but optionally included in system 110, may be a controller 118 and one or more sensors 119.

In any of the embodiments described herein, thermal energy transmission member 113 may include two heat delivery members, one configured for positioning over at least part of the popliteal fossa and one configured for positioning over at least part of the sole of the foot. Alternative embodiments may include fewer or more thermal energy transmission members 113, and these embodiments may be configured for positioning on other anatomical locations on the patient. Regulating temperature at the popliteal fossa and sole of the foot, however, may be a very effective and efficient way to regulate a patient's body temperature. In these embodiments, blood flow regulation member 112 may be one intermittent compression delivery member, configured for positioning on the patient's lower limb between the two thermal energy transmission members 113 on the foot and the popliteal fossa. For example, blood flow regulation member 112 may be positioned on the calf. This combination of thermal energy delivery to the popliteal fossa and sole of the foot, along with intermittent compression delivery to the calf, may be a very effective way to increase and/or maintain a patient's body temperature and thus prevent inadvertent perioperative hypothermia.

The embodiment of FIG. 4 may have a number of advantages over an embodiment having a multi-piece body interface member. For example, it may be easier to apply and remove one body interface member 111, as compared to multiple members. Additionally, it is possible to use only one connector 114 in such an embodiment, since thermal energy and/or intermittent compression force may be transferred through body interface member 111 to thermal energy transfer member(s) 113 and blood flow regulation member(s) 112. On the other hand, in some cases it may be advantageous to have several, separate body interface members 101 (FIG. 3), with separate components attached to each. For example, it may be easier to apply and remove smaller, separate body interface members 101. In some cases, it may be desirable to use only a subset of the separate components, either by themselves or in conjunction with another device, such as a currently available intermittent compression or heat delivery device. Therefore, various different embodiments may be advantageous in different circumstances.

Figure 5:
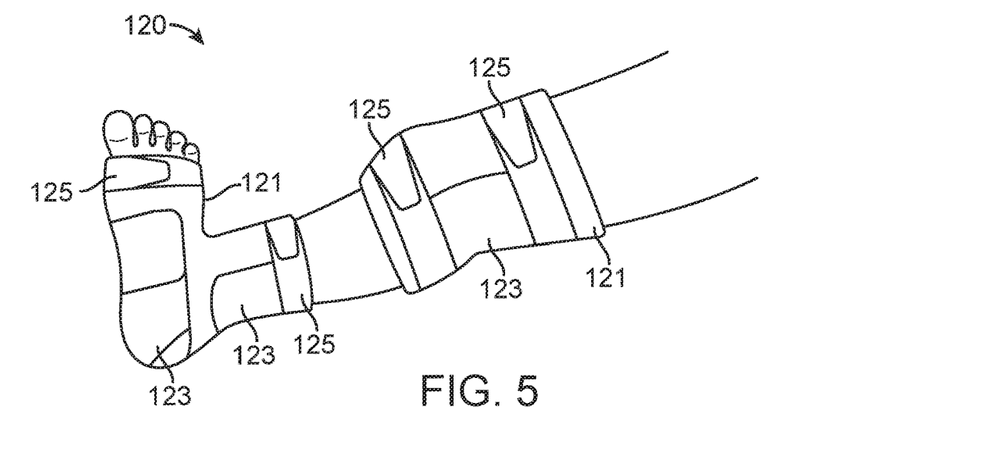
FIG. 5 is a perspective view of a lower limb of a human with a body temperature regulation system in place on the lower limb, according to another alternative embodiment.

With reference now to FIG. 5, another alternative embodiment of a body temperature regulation system 120 may include two body interface members 121, each of which is coupled with one or more thermal energy transfer members 123 and is secured to the patient via one or more straps 125. Thermal energy transfer members 123 are housed in separate body interface members 121—one for the popliteal fossa and one for the sole of the foot and ankle. These components may be used together, separately, or with and other components herein. Obviously, system 120 is not illustrated with any connectors or central units, but these may be provided as part of system 120 or may be part of another system with which system 120 may be used. In one embodiment, system 120 illustrated in FIG. 5 may be the same as system 100 illustrated in FIG. 3, except without blood flow regulation member 102.

Figure 6:
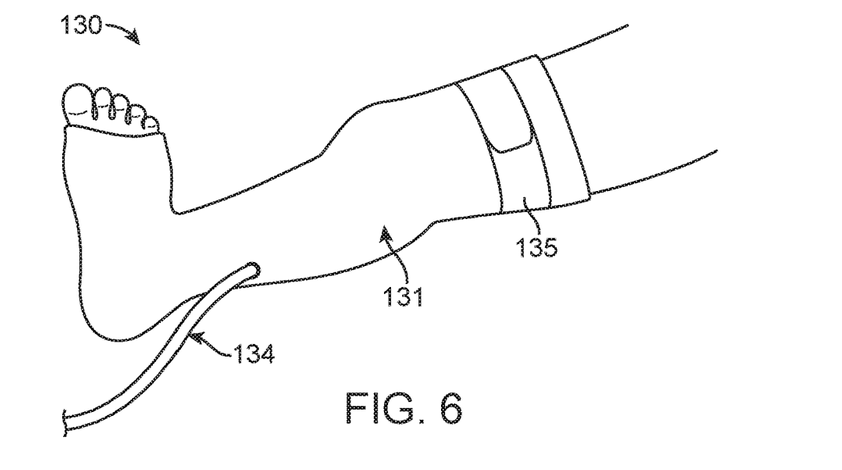
FIG. 6 is a perspective view of a lower limb of a human with a body temperature regulation system in place on the lower limb, according to another alternative embodiment.

Referring now to FIG. 6, in another alternative embodiment, a body temperature regulation system 130 may include a thermal energy transfer sock 131, coupled with a connector 134 and attached to the lower limb via a strap 135. Connector 134, of course, may be coupled with a central unit, controller, or combined central unit/controller, as described above but not illustrated here. In this embodiment, system 130 does not include a blood flow regulation member. However, sock 131 may be combined with a blood flow regulation members, such as an intermittent compression device, in some embodiments. For example, a compression device may be applied over sock 131 in some embodiments. Sock 131 may be made of any suitable material, such as but not limited to those listed above in reference to the various embodiments of body interface members.

Figure 7:
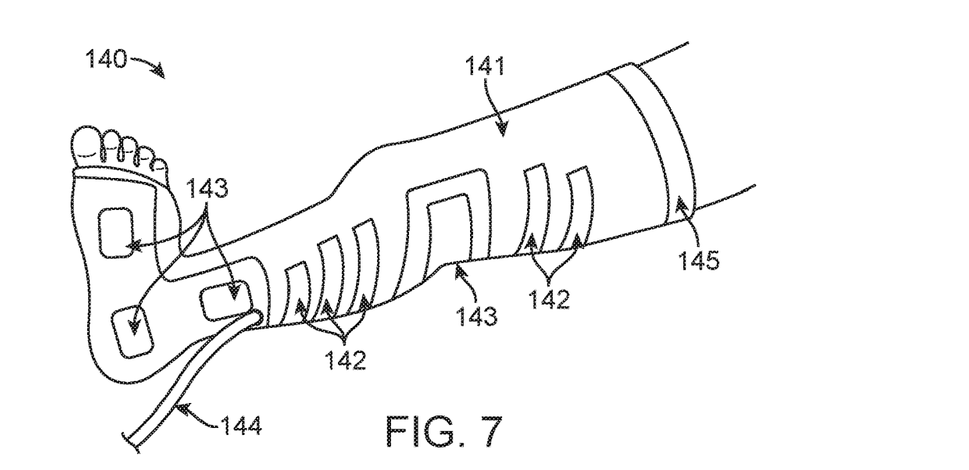
FIG. 7 is a perspective view of a lower limb of a human with a body temperature regulation system in place on the lower limb, according to another alternative embodiment.

With reference to FIG. 7, yet another alternative embodiment of a body temperature regulation system 140 may include a body interface member 141 attached to the limb via one or more straps 145, multiple thermal energy transfer members 143, and multiple blood flow regulation members 142. In this embodiment, multiple thermal energy transfer members 143 are positioned on the sole of the foot and behind the ankle, and another thermal energy transfer member 143 is positioned at the popliteal fossa. Blood flow regulation members 142 are configured as strips, and each strip houses one or more electrodes, which are used to stimulate tissue and promote muscle contraction. These electrode strips are positioned both above and below the popliteal fossa, although in alternative embodiments only one set of strips in one location may be used.

Figure 8:
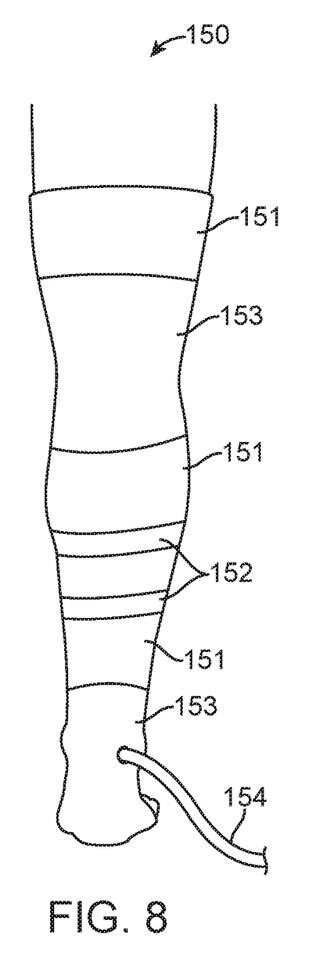
FIG. 8 is a posterior view of a lower limb showing another alternative embodiment of a body temperature regulating system.

FIG. 8 is a posterior view of a lower limb showing another alternative embodiment of a body temperature regulating system 150. In this embodiment, system 150 includes a body interface member 151 that fits over most or all of the lower limb, blood flow regulation member 152 comprising two strips of electrodes, a thermal energy transfer member 153 comprising two heat transfer elements, and a connector 154. Various features, details and alternatives described above in relation to other embodiments may be applied to this embodiment as appropriate.

Figure 9:
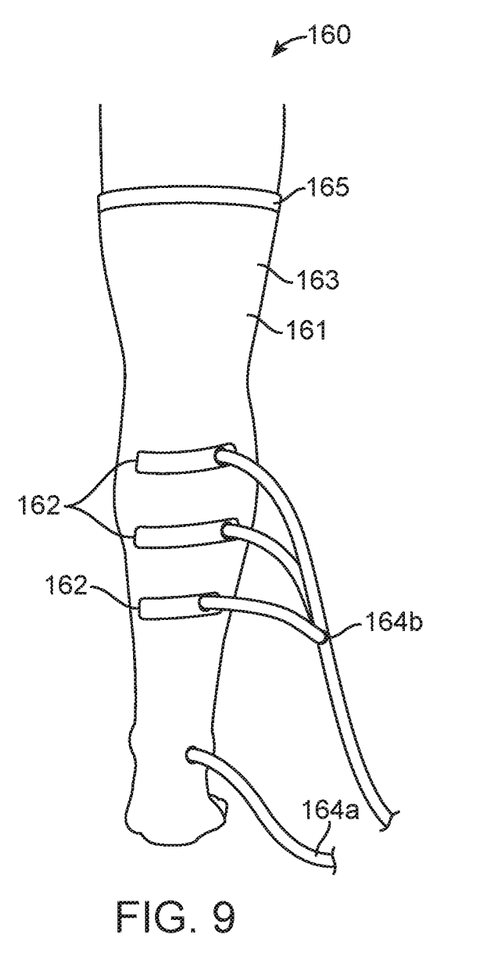
FIG. 9 is a posterior view of a lower limb showing another alternative embodiment of a body temperature regulating system.

FIG. 9 is a posterior view of a lower limb showing another alternative embodiment of a body temperature regulating system 160. In this embodiment, system 160 includes a body interface member 161 that fits over most or all of the lower limb and that acts as a thermal energy transfer member 163, similar to (or identical to) the embodiment described above as a heat transfer sock. System 160 also includes a blood flow regulation member 162 comprising three strips of electrodes, a first connector 164a leading to thermal energy transfer member 163, and a second set of connectors 164b leading to blood flow regulation members 162. Various features, details and alternatives described above in relation to other embodiments may be applied to this embodiment as appropriate.

Figure 10:
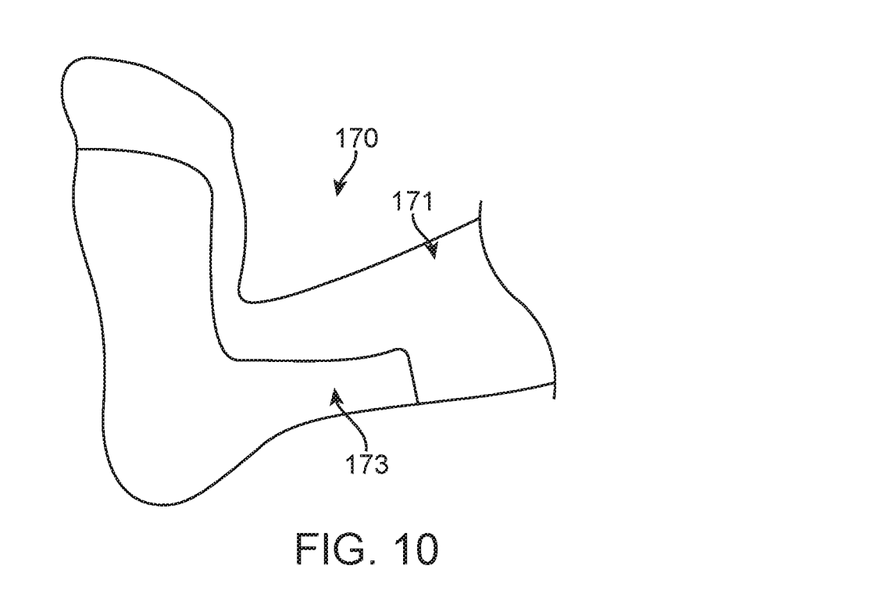
FIG. 10 illustrates one embodiment of a foot-positioned component of a body temperature regulation system.

FIG. 10 illustrates one embodiment of a foot-positioned component 170 of a body temperature regulation system. In this embodiment, component 170 includes a body interface member 171, such as a sock-like member, and a thermal energy transfer member 173. Thermal energy transfer member 173 does not cover all of the foot in this embodiment but is disposed over a portion of the sole of the foot and the back of the ankle.

Figure 11:
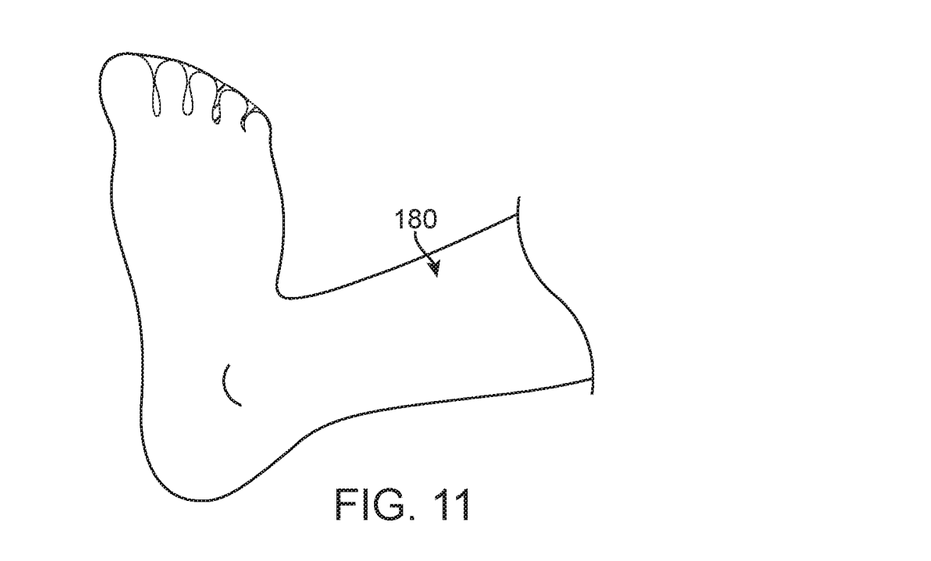
FIG. 11 illustrates an alternative embodiment of a foot-positioned component of a body temperature regulation system.

FIG. 11 illustrates an alternative embodiment, in which a foot-positioned component 180 of a body temperature regulation system comprises a combined, sock-like body interface and thermal energy transfer member.

Figure 12:
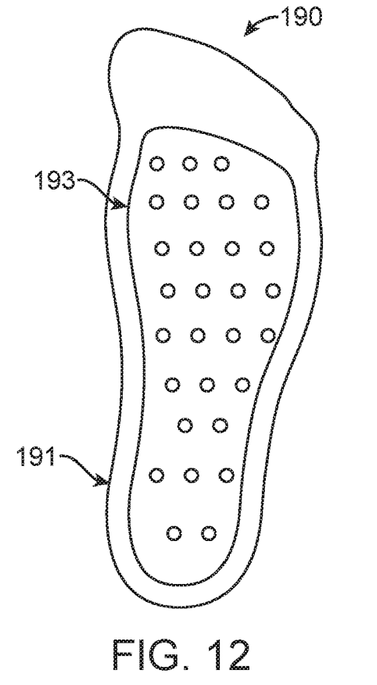
FIGS. 12-15 are bottom views of a sole of a foot, illustrating various alternative embodiments of a foot-positioned component of a body temperature regulating system.
Figure 13:
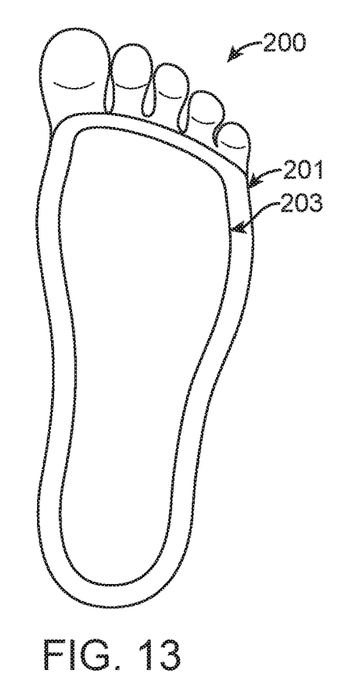
Figure 14:
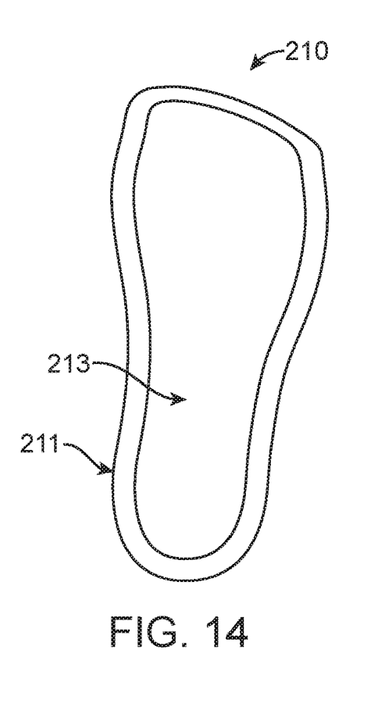
Figure 15:
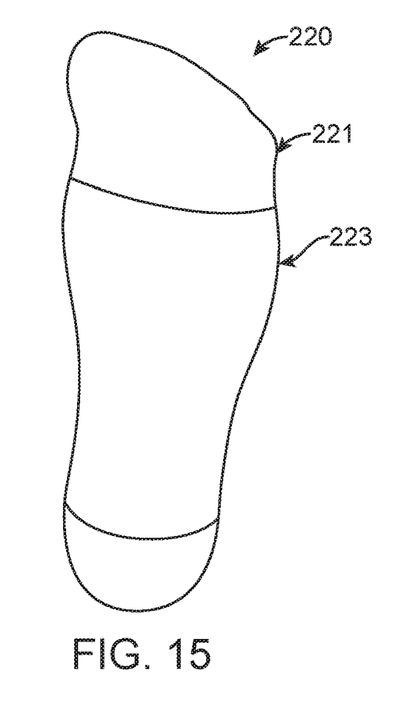

FIGS. 12-15 are bottom views of a sole of a foot, illustrating various alternative embodiments of a foot-positioned component 190, 200, 210, 220 of a body temperature regulating system. In each embodiment, foot-positioned component 190, 200, 210, 220 includes a body interface component 191, 201, 211, 221 and a thermal energy transfer component 193, 203, 213, 223. As these figures illustrate, any of a number of different configurations may be used in various embodiments of a foot-positioned of a body temperature regulating system. Specifically, various embodiments may be configured to help ensure comfort and/or facilitate a patient's ability to walk while using the system. For example, as illustrated in the embodiment of FIG. 12, a bottom surface of thermal energy transfer unit 193 (or additionally or alternatively body interface member 191) may include tacky or gripping materials on the soles of the feet or palms of the hand to ensure safety and function during use.

Figure 16A:
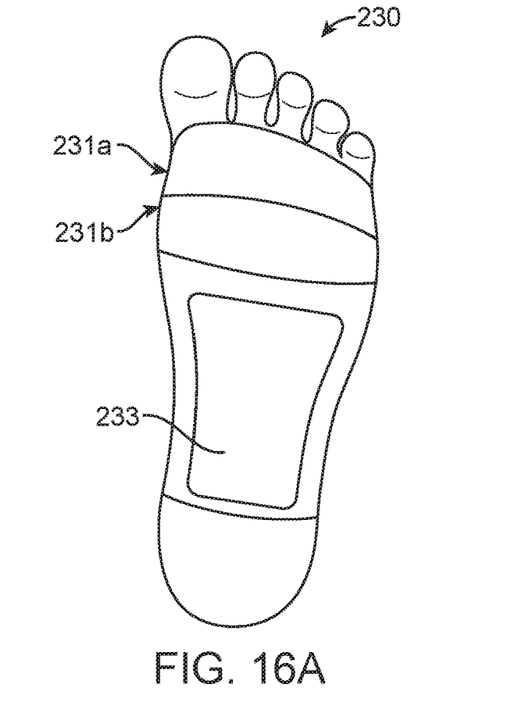
FIGS. 16A and 16B are bottom views of a sole of a foot, illustrating another alternative embodiment of a foot-positioned component of a body temperature regulating system.
Figure 16B:
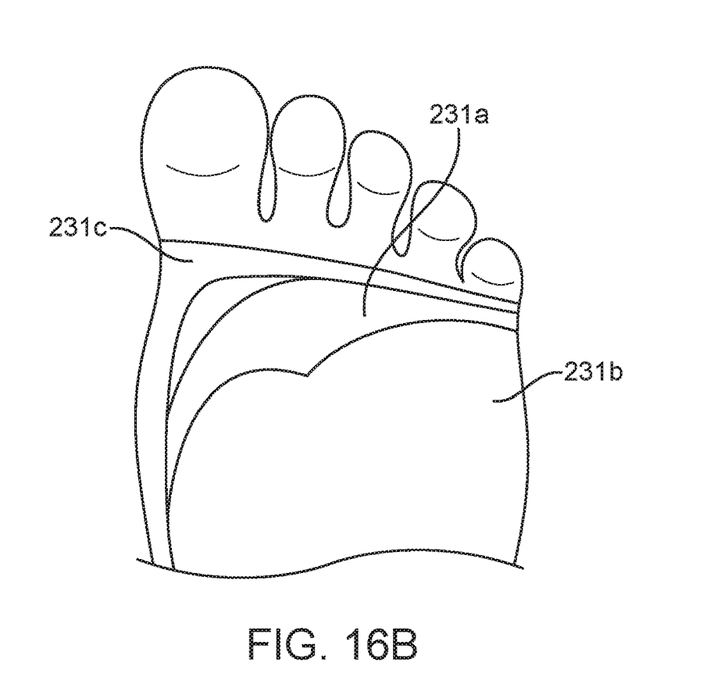

FIGS. 16A and 16B are bottom views of a sole of a foot, illustrating another alternative embodiment of a foot-positioned component 230 of a body temperature regulating system. In this embodiment, foot-positioned component 230 includes a body interface component that has multiple layers 231a, 231b, 231c and a thermal energy transfer component 233. The various layers 231a, 231b, 231c may be made of any suitable, conformable material, such as but not limited to those previously listed above.

As mentioned previously, any individual component of the system embodiments described above may be located in a single location or combination of locations. These locations may include those on the body of mammals. As described previously, the thermal energy transfer component may be located continuously along the extremity or in separate locations ideal for thermal energy transfer. These may include locations where there is high blood flow, where the artery or vein is close to the skin surface, and/or where there is little interference with required clinical access. These include, but are not limited to, the hands, feet, neck, and major arteries and veins of the extremities including the femoral, popliteal, saphenous, tibial, pedal, axillary, brachial, cubital, radial, ulnar, cephalic, jugular, carotid arteries and veins. Blood flow regulator components may be placed in any single or combination of locations to regulate blood flow of the arteries and veins described above.

Any of a number of embodiments of methods for regulating body temperature may be performed, using the systems described above. These methods may be used not only for the prevention of hyperthermia, but also for the maintenance of normothermia, the maintenance of therapeutic hypothermia, the maintenance of therapeutic hyperthermia, the recovery from hypothermia in both environments internal and external to the hospital, and/or recovery from hyperthermia in both environments internal and external to the hospital. For example, in one embodiment, a method may involve positioning a thermal energy transfer member over at least part of the popliteal fossa and at least part of the sole of the foot, positioning an intermittent compression member or other blood flow regulation member in an area of the lower limb between the two thermal energy transfer members, and providing heat and compression force to the lower limb using the system.

Various embodiments of these methods for body temperature regulation may involve, for example: (1) Transferring thermal energy and/or regulating blood flow for the control of core body temperature through the extremities, including but not limited to the arms, legs, face, palm of the hand, sole of the foot, neck and head; (2) Transferring thermal therapy in conjunction with or independently of blood flow regulation therapy prior to induction of anesthesia. The thermal therapy may continue in conjunction with or independently of blood flow regulation therapy after the induction of anesthesia; Transferring thermal energy and/or regulating blood flow continuously or intermittently, including random or patterned application. (4) Transferring thermal energy and/or regulating blood flow at varied time intervals, which may or may not be in synchronization with one another; (6) Transferring thermal energy preoperatively in order to prevent hypothermia before induction of anesthesia and after induction due to redistribution hypothermia; (7) Transferring thermal energy preoperatively as described above and continuing thermal energy transfer and/or blood flow regulation in intraoperative and/or postoperative settings; and/or (8) Transferring thermal energy and/or regulating blood flow for the control of core body temperature in order to benefit patients with or at risk of lymphedema, deep vein thrombosis, peripheral artery disease, muscle conditions, or any other suitable condition.

Although this invention has been described in detail, the scope of the invention as set forth in the following claims should not be limited by the foregoing descriptions of various embodiments. Thus, it is intended that the scope of the present invention herein disclosed should not be limited by the particular disclosed embodiments described above, but should be determined only by a fair reading of the claims that follow.

We claim:

1. A method of managing temperature of a patient, the method comprising:
   providing a sleeve device, the sleeve device comprising:
   a first portion configured to cover only a popliteal fossa of a lower limb of the patient;
   a first electrical heating device associated with the first portion;
   a second portion configured to cover at least a portion of a sole of a foot of the lower limb;
   a second electrical heating device associated with the second portion;
   a third portion disposed between the first portion and the second portion, the third portion being configured to wrap at least partially around a calf of the lower limb; and
   one or more intermittent compression devices associated with the third portion;
   placing the sleeve device at least partially on the lower limb of the patient, said placing the sleeve device involving:
   bringing the first portion into contact with only the popliteal fossa;
   bringing the second portion into contact with the sole of the foot; and
   bringing the third portion into contact with the calf;
   delivering heat to the popliteal fossa using the first electrical heating device;
   delivering heat to the sole of the foot using the second electrical heating device; and
   applying intermittent compression to the calf using the one or more intermittent compression devices;
   wherein said delivering heat to the popliteal fossa and the sole of the foot and applying intermittent compression increases a core body temperature of the patient.

2. The method of claim 1, wherein the first electrical heating device and the second electrical heating device are longitudinally movable along the sleeve device.

3. The method of claim 1, wherein the one or more intermittent compression devices include at least one of the group consisting of:
electrode strips configured to stimulate tissue and promote muscle contraction; and
fluid-fillable pressure chambers.

4. The method of claim 1, wherein the sleeve device comprises one or more electrode strips associated with a fourth portion of the sleeve device that is configured to cover a portion of a back of the lower limb that is above the popliteal fossa.

5. The method of claim 1, wherein said delivering heat to the popliteal fossa is performed independently of said applying intermittent compression to the calf.

6. The method of claim 1, wherein said delivering heat to the popliteal fossa and said delivering heat to the sole of the foot are not synchronized with one another.

7. A method as in claim 1, wherein said applying intermittent compression to the calf involves electrically stimulating the calf using the one or more intermittent compression devices.

8. A temperature-management device comprising:
a sleeve configured for placement over at least a portion of a sole of a foot, a calf, and a popliteal fossa of a lower limb of a patient, the sleeve including a first compartment and a second compartment;
a first electrical heating device placed in the first compartment such that the first electrical heating device is positioned to cover only the popliteal fossa when the sleeve is placed over the popliteal fossa;
a second electrical heating device placed in the second compartment such that the second electrical heating device is positioned over the sole of the foot when the sleeve is placed over the sole of the foot; and
an intermittent compression device coupled with the sleeve such that the intermittent compression device is positioned over at least a portion of the calf when the sleeve is placed over the calf.

9. The temperature-management device of claim 8, wherein the first heating device and the second heating device are configured to deliver thermal energy in a form selected from the group consisting of ultrasound, electrical, mechanical, chemical, radiative and convective energy.

10. The temperature-management device of claim 8, wherein the intermittent compression device is configured to apply pressure to the calf in a form selected from the group consisting of electrical stimulation, mechanical compression, and mechanical torsion of the lower limb.

11. The temperature-management device of claim 8, wherein the intermittent compression device comprises at least one expandable bladder.

12. The temperature-management device of claim 8, further comprising:
a controller coupled with the sleeve and configured to control at least one of heat delivery or compression application by the device;
at least one temperature sensor configured to sense a temperature of the patient when the sleeve is placed over at least a portion of the lower limb of the patient; and
a connection between the at least one temperature sensor and the controller configured to provide sensed temperature data to the controller.

13. The temperature-management device of claim 12, wherein the controller is further configured to control the first and second heating devices and the intermittent compression device based at least in part on the sensed temperature data.

14. The temperature-management device of claim 8, wherein the sleeve comprises multiple compartments, and wherein the first heating device, the second heating device, and the intermittent compression device are disposed in respective ones of the multiple compartments.

15. The temperature-management device of claim 8, wherein at least one of the first heating device, the second heating device, or the intermittent compression device is longitudinally moveable.

16. The temperature-management device of claim 8, further comprising a wicking material on an inner surface of at least part of the sleeve.

17. The temperature-management device of claim 8, wherein at least part of the intermittent compression device is positioned above the popliteal fossa when the sleeve is placed over the popliteal fossa.

18. The temperature-management device of claim 8, further comprising an adhesive on at least a portion of an inner surface of the sleeve that is configured to provide adhesion between the inner surface and skin of the lower limb.

19. A device for increasing core body temperature of a patient, the device comprising:
a sleeve configured for placement over at least a portion of a sole area of a foot, a calf, and a popliteal fossa area of a lower limb of a patient;
a first electrical heating device coupled with the sleeve such that the first electrical heating device is positioned over and limited to cover only the popliteal fossa area when the sleeve is placed over the popliteal fossa;
a second electrical heating device coupled with the sleeve such that the second electrical heating device is positioned over and limited to cover only the sole of the foot when the sleeve is placed over the sole of the foot; and
an intermittent compression device coupled with the sleeve such that the intermittent compression device is positioned over at least a portion of the calf when the sleeve is placed over the calf;
wherein the first electrical heating device and the second electrical heating device are the only heating devices associated with the sleeve.

* * * * *